United States Patent [19]

Deaton

[11] Patent Number: 5,220,030
[45] Date of Patent: Jun. 15, 1993

[54] PHOTOGRAPHIC SILVER HALIDE MATERIAL COMPRISING GOLD COMPOUND

[75] Inventor: Joseph C. Deaton, Rochester, N.Y.

[73] Assignee: Eastman Kodak Company, Rochester, N.Y.

[21] Appl. No.: 699,076

[22] Filed: May 13, 1991

Related U.S. Application Data

[62] Division of Ser. No. 614,536, Nov. 16, 1990, Pat. No. 5,049,485.

[51] Int. Cl.⁵ .............................................. C07D 249/10
[52] U.S. Cl. ...................................... 548/105; 430/605
[58] Field of Search ...................... 548/105; 430/605

[56] References Cited

U.S. PATENT DOCUMENTS

| | | | |
|---|---|---|---|
| 2,597,856 | 5/1952 | Damschroder | 95/7 |
| 2,597,915 | 5/1952 | Yutzy et al. | 95/7 |
| 3,503,749 | 3/1970 | Tavernier et al. | 96/107 |
| 4,163,669 | 8/1979 | Kanada et al. | 96/74 |
| 4,378,424 | 3/1983 | Altland et al. | 430/352 |
| 4,404,390 | 9/1983 | Altland et al. | 548/263 |
| 4,772,545 | 9/1988 | Nishiyama et al. | 430/564 |
| 4,810,626 | 3/1989 | Burgmaier et al. | 430/569 |
| 4,906,558 | 3/1990 | Muke et al. | 430/550 |

OTHER PUBLICATIONS

G. E. Coates, B. Kowala & J. M. Swan; Coordination Compounds of Group IB Metals J. Chem., 19, Aug. 1966, pp. 539–545.

*Primary Examiner*—Nicholas S. Rizzo
*Attorney, Agent, or Firm*—Paul A. Leipold

[57] ABSTRACT

A photographic silver halide material is chemically sensitized with a soluble gold(I) compound of the formula:

$$AuL_2^+ X^-$$

or $$AuL(L^1)^+ X^-$$

wherein L is a mesoionic compound; X is an anion; and $L^1$ is Lewis donor ligand. The novel gold(I) compounds possess properties which are advantageous compared to the properties of previously known gold compounds.

8 Claims, No Drawings

PHOTOGRAPHIC SILVER HALIDE MATERIAL COMPRISING GOLD COMPOUND

This is a divisional of application Ser. No. 614,536, filed Nov. 16, 1990, now U.S. Pat. No. 5,049,485.

This invention relates to new gold(I) compounds comprising mesoionic ligands and to photographic silver halide materials chemically sensitized with such gold(I) compounds.

Photographic silver halide materials are often chemically sensitized with one or more compounds containing labile atoms of gold, sulfur or selenium and the like to provide increased sensitivity to light and other sensitometric properties. Examples of typical chemically sensitized photographic silver halide emulsions are described in, for example, Research Disclosure, Item No. 308119, December 1989, Section III, and the references listed therein (Research Disclosure is published by Kenneth Mason Publications Ltd., Dudley Annex, 12a North Street, Emsworth, Hampshire PO 10 7DQ, England.)

Gold compounds may contain gold in the (I) or (III) oxidation state. However, those in the (I) oxidation state are preferred because those gold compounds in the (III) oxidation state may undergo side reactions that, for example, oxidize gelatin or other components in photographic emulsions. Among gold(I) compounds, trisodium aurous dithiosulfate is commonly known as a chemical sensitizer, but is not universally applicable because of the disadvantages this compound provides. In particular, this gold(I) compound contains two thiosulfate ions that are bonded to gold. These ions may also undergo sensitization reactions in addition to the gold in a photographic silver halide emulsion. Therefore, this gold(I) compound is not appropriate in silver halide compositions in which an amount of sulfur less than a 2:1 molar ratio with gold is desired in for chemical sensitization, and not appropriate in silver halide compositions in which sulfur or selenium sensitizers other than thiosulfate are desired, such as a silver halide composition as described containing thioureas in U.S. Pat. No. 4,810,626 of Burgmaier et al.

Gold(I) compounds are known that do not contain thiosulfate ligands or other ligands possessing labile sulfur. However, many such gold(I) compounds are not useful as chemical sensitizers for photographic silver halide materials because their dissociation constants are too high and provide low stability. Such gold(I) compounds are susceptible to disproportionation or reduction by gelatin components, especially those in photographic silver halide emulsions. Many gold(I) compounds are not sufficiently soluble to be easily dispersed in a photographic silver halide composition in a uniform and controllable manner.

One gold(I) compound that has been proposed is a gold(I) thiolate as described in U.S. Pat. No. 3,503,749 of Tavernier et al. This compound contains a sulfonic acid sodium salt substituent on the thiolate ligand to impart water solubility. However, the process for preparing such gold(I) compounds involves use of gold fulminate that is dangerously explosive and thus not desirable for practical use.

Other gold(I) compounds, such as those containing alkyl or aryl thiolate ligands are also not useful because the alkyl or aryl thiolate may be readily displaced from the gold compound by protons, as described in, for example, G. E. Coates, B. Kowala and J. M. Swan; *Aust. J. Chem.*, 19, 539 (1966).

It has been desirable to provide a new gold(I) compound that enables chemical sensitization of photographic silver halide compositions for increased light sensitivity without undesired side reactions. It has also been desirable to provide such new gold(I) compounds that are sufficiently soluble and stable for use in photographic silver halide compositions and are easy to prepare without involving dangerous intermediates.

It has been found that the described advantages are provided by a photographic silver halide emulsion, preferably a gelatin emulsion, chemically sensitized with a gold(I) compound of the formula:

$$AuL_2^+X^-$$

or $$AuL(L^1)^+X^-$$

wherein
L is a mesoionic compound;
X is an anion; and
$L^1$ is a Lewis donor ligand.

The compounds may be soluble in any of a variety of solvents, including water or organic solvents such as acetone or methanol, but the most preferred compounds are water soluble. The term water soluble herein means that the gold(I) compound dissolves in water at the concentration of at least $10^{-5}$ mole per liter of water at a temperature of 20° C. at normal pressure.

The mesoionic compound L herein is any such compound that can be coordinated with gold(I) ions to form a gold(I) compound that is water soluble and enables the described chemical sensitization of a photographic silver halide composition. The mesoionic compound is preferably represented by the formula:

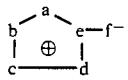

wherein the circle with the + sign on the heterocyclic ring symbolizes six delocalized π electrons associated with a partial positive charge on the heterocyclic ring. The a, b, c, d, and e represent the unsubstituted or substituted atoms necessary to complete the mesoionic compound, for example the carbon and nitrogen atoms necessary to complete a mesoionic triazolium or tetrazolium 5-member heterocyclic ring. The members of the heterocyclic ring (a, b, c, d, and e) may be CR or NR' groups or chalcogen atoms. The minus sign indicates two additional electrons on the exocyclic group f which are conjugated with the six π electrons on the heterocyclic ring. It is understood that there is extensive delocalization and that the charges indicated are only partial charges. The exocyclic group f may be S, Se, or NR". The groups R, R' and R" may be hydrogen atoms, substituted or unsubstituted alkyl, aryl, or heterocyclic groups, or R, R' and R" may link together by bonding to form another ring. (Note: Structural representations for mesoionic compounds L which are different from that given above appear elsewhere in the literature, but here the conventions followed are those described by Ollis and Ramsden in *Advances in Heterocyclic Chemistry*, Vol. 19, Academic Press, London (1976). It is through the exocyclic group f that the mesoionic compound coordinates to gold (I) in the novel compounds of the present invention. The exocyclic group f should not be 0 for the present invention since oxygen ligands are not known to form stable compounds with gold (I).

Examples of the gold (I) compounds of the invention are given in the table below. In the structural representations of the gold (I) compounds, the partial charges on the mesoionic ligands are dropped to avoid confusion with the overall charge of the complex ion. The rings symbolizing six delocalized $\pi$ electrons on the heterocyclic moieties are retained, but will be understood not to imply aromaticity.

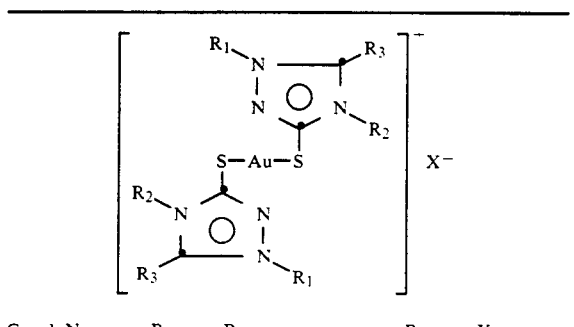

| Cmpd. No. | $R_1$ | $R_2$ | $R_3$ | $X^-$ |
|---|---|---|---|---|
| 1 | $CH_3$ | $CH_3$ | $CH_3$ | $BF_4^-$ |
| 2 | $CH_3$ | $CH_3$ | $CH_3$ | $I^-$ |
| 3 | $CH_3$ | $CH_3$ | $CH_3$ | $Br^-$ |
| 4 | $CH_3$ | $CH_3$ | $CH_3$ | $Cl^-$ |
| 5 | $CH_3$ | $CH_2CH=CH_2$ | $CH_3$ | $BF_4^-$ |
| 6 | $CH_3$ | $CH_2CH_2OCH_3$ | $CH_3$ | $BF_4^-$ |
| 7 | $CH_3$ | $NH_2$ | $CH_3$ | $BF_4^-$ |
| 8 | $CH_3$ | $C_4H_9$ | $CH_3$ | $BF_4^-$ |
| 9 | $CH_3$ | $C_6H_{11}$ | $CH_3$ | $BF_4^-$ |
| 10 | $CH_3$ | $C_6H_5$ | $C_6H_5$ | $BF_4^-$ |

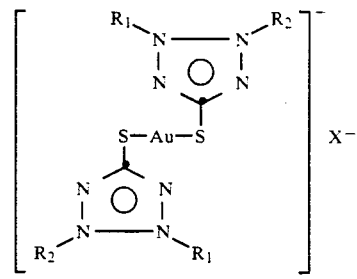

| Cmpd. No. | $R_1$ | $R_2$ | $X^-$ |
|---|---|---|---|
| 11 | $C_6H_5$ | $C_6H_5$ | $BF_4^-$ |

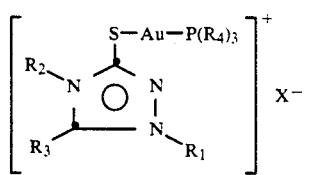

| Cmpd. No. | $R_1$ | $R_2$ | $R_3$ | $R_4$ | $X^-$ |
|---|---|---|---|---|---|
| 12 | $CH_3$ | $CH_3$ | $CH_3$ | $CH_3$ | $Cl^-$ |
| 13 | $CH_3$ | $CH_3$ | $CH_3$ | $CH_3$ | $BF_4^-$ |
| 14 | $CH_3$ | $CH_2CH=CH_2$ | $CH_3$ | $CH_3$ | $BF_4^-$ |

These novel gold (I) compounds are advantageous over certain other gold compounds containing sulfur known in the art such as trisodium aurous dithiosulfate because the novel compounds do not contain any labile S atoms, thus allowing independent choice and amount of S sensitizer, which is not possible with trisodium aurous dithiosulfate. The flexibility in choice and amount of sulfur sensitizer to be used in photographic emulsion is necessary in some cases to achieve proper gradation, reduced sensitivity to red light, and other sensitometric properties. The compounds of the present invention also are advantageous over other soluble gold(I) compounds which do not contain labile S atoms because the novel compounds have a lower dissociation constant and consequently have better solution stability. Alkyl or aryl thiolates, for example, have a propensity to form polymeric gold(I) compounds with a 1:1 thiolate to gold formula. The compounds of this invention contain discrete gold(I) complexes possessing two ligands. Consequently, the novel compounds have solubility properties which are convenient for dispersion in the emulsion without requiring that a sulfonic acid or other solubilizing group be attached to the ligand. The novel compounds of the present invention also are advantageous over prior art gold(I) compounds in that the preparation and purification of the compounds is very convenient and does not involve potentially explosive material.

The mesoionic compounds L used as starting materials to form the novel compounds with gold(I) may be made by methods described by Altland, Dedio and McSweeney, U.S. Pat. No. 4,378,424 (1983) or by methods described in the review article by Ollis and Ramsden cited above and references given therein. Synthesis of the novel gold(I) compounds can be effected by various techniques known to the art. One convenient method comprises reacting a gold(I) precursor compound with an appropriate amount of the mesoionic compound. In the ensuing reaction, which generally takes place within a few minutes at room temperature (about 20° C.) or slightly above, the ligands of the gold(I) precursor compound are displaced by the mesoionic compounds, which have a higher affinity for gold(I). The product may then be isolated and purified by crystallization techniques.

The various substituent groups on the mesoionic compound modify the solubility of the final product gold(I) compound. The most desired gold(I) compounds are those which are soluble in water and which may be made in water. Those which are soluble in organic solvents such as acetone can still be used to sensitize aqueous emulsions, and can be used to sensitize emulsions in non-aqueous media.

This invention also provides a process for sensitizing a silver halide emulsion formed according to processes generally well-known in the art. A double jet-type process is preferred. The silver halide grains can comprise mixed or single halide components and especially include chloride, bromide, iodide, iodochloride, iodobromide or chlorobromide grains.

The double-jet process comprises adding an aqueous silver nitrate solution and an aqueous solution of one or more halides, for example, an alkali metal halide such as potassium bromide, potassium chloride, potassium iodide or mixtures thereof, simultaneously to a stirred solution of a silver halide protective colloid through two separate jets.

In the present invention, the described sensitizing gold(I) compounds may be added to a silver halide emulsion at various stages during its preparation. For example, the compounds may be added at levels from about $10^{-7}$ to about $10^{-3}$ mol thereof per mol of silver halide. A preferred concentration of gold compound to achieve sensitization of silver halide is from about $10^{-6}$ to about $10^{-4}$ mol thereof per mol of silver halide.

The gold sensitizing compounds may be added singly or in combination with other sensitizing agents. They may also be added to a silver halide emulsion along with silver ion ligands and silver halide growth modifiers or stabilizers and antifogging agents, or with spectral or chemical senitizing agents such as sulfur or selenium compounds or with dopants such as iridium complexes, during formation of silver halide grains, during the physical or chemical ripening stage, or in a separate step before coating.

Conditions for sensitizing silver halide grains such as pH, pAg, temperature, etc., are not particularly limited when employed using compounds described herein. The pH is generally about 1 to 9, preferably about 3 to 6, and pAg is generally about 5 to about 12, preferably from about 7 to about 10. Silver halide grains may be sensitized at temperatures between about 30° to about 90° C., with about 40° to about 70° C. being preferred.

Gelatin is preferred as the binder or protective colloid for the photographic emulsion of the present invention. However, other hydrophilic colloids are also suitable. For example, proteins such as gelatin derivatives, graft polymers of gelatin and other polymers, albumin, casein, cellulose derivatives such as hydroxyethyl cellulose, carboxymethyl cellulose and cellulose sulfate, sugar derivatives such as sodium alginate, starch derivatives and various synthetic peptizers such as hydrophilic homopolymers or copolymers such as polyvinyl alcohol, poly-N-vinylpyrrolidone, polyacrylic acid, polymethacrylic acid, polyacrylamide, polyvinylimidazole and polyvinyl pyrazole can be used.

Acid-processed gelatin can be used, as well as lime-processed gelatin. Further, gelatin hydrolyzates and enzyme-hydrolyzed products of gelatin are also usable.

Surface-active agents may be incorporated in a photographic emulsion layer or in another hydrophilic colloid layer as a coating aid to prevent build-up of static charge, to improve lubrication properties, to improve emulsion dispersion, to prevent adhesion and to improve other properties.

A photosensitive material of the present invention may contain antifogging agents or emulsion-stabilizing agents such as, for example, azaindenes, thionamides, azoles and the like.

The photographic silver halide emulsions as described can be used in photographic silver halide elements in any of the ways and for purposes known in the photographic art.

The photogrpahic silver halide emulsions can be used and incorporated in photographic elements that are single color elements or multicolor elements. Multicolor elements contain dye image-forming units sensitive to each of the three primary regions of the visible spectrum. Each unit can be comprised of a single emulsion layer or of multiple emulsion layers sensitive to a given region of the spectrum. The layers of the element can be arranged in various orders as known in the art.

In the following discussion of suitable materials for use in emulsions and elements of the invention, reference will be made to Research Disclosure, December 1989, Item No. 308119. Research Disclosure is published by Kenneth Masons Publications Ltd., Dudley Annex, 12a North Street, Emsworth, Hampshire PO 10 7DQ, England. This publication will be identified hereafter by the term "Research Disclosure".

The silver halide emulsions of the invention can be used in elements that can be either negative-working or positive-working. The emulsions in which the described new chemical sensitizers can be used are described in, for example, Research Disclosure Sections I, II and III and the publications and patents cited therein. Useful vehicles for the emulsion layers and other layers of elements of the invention are described in Research Disclosure Section IX and the publications cited therein.

The described photographic emulsions can be used in color photographic elements with couplers as described in Research Disclosure Section VII and the publications cited therein. The couplers can be incorporated in the elements and emulsions as described in Research Disclosure Section VII and ways known in the art.

The photographic elements and emulsions as described can contain addenda known to be useful in photographic elements and emulsions in the photographic art. The photographic elements and emulsions as described can contain, for example, brighteners (see Research Disclosure Section V); antifoggants and stabilizers (see Research Disclosure Section VI); antistain agents and image dye stabilizers (see Research Disclosure Section VII); light absorbing and scattering materials (see Research Disclosure Section VIII); hardeners (see Research Disclosure Section X); coating aids (see Research Disclosure Section XI); plasticizers and lubricants (see Research Disclosure Section XII); antistatic agents (see Research Disclosure Section XIII); matting agents (see Research Disclosure Section XVI); and development modifiers (see Research Disclosure Section XXI).

The photographic silver halide materials and elements as described can be coated on a variety of supports as described in Research Disclosure Section XVII and the publication cited therein.

The photographic silver halide materials and elements as described can include coarse, regular and fine grain silver halide crystals or mixtures thereof and can be comprised of any photographic silver halides known in the photographic art.

The photographic silver halide materials as described can be spectrally sensitized by means and dyes known in the photographic art, such as by means of spectral sensitizing dyes as described in, for example, Research Disclosure Section IV and the publications cited therein. Combinations of spectral sensitizing dyes are especially useful.

Photographic materials and elements as described can be exposed to actinic radiation, typically in the visible region of the spectrum, to form a latent image as described in Research Disclosure Section XVIII and then processed to form a visible image as described in, for example, Research Disclosure Section XIX using developing agents and other processing agents known in the photographic art. Processing to form a visible image, typically a dye image, includes the step of contacting the element with a developing agent, typically a color developing agent, to reduce developable silver halide and oxidize the developing agent. In a color material the oxidized color developing agent in turn reacts with couplers to yield a dye.

The photographic silver halide materials can also be used in physical development systems as described in Research Disclosure Section XXII, in image-transfer systems as described in Research Disclosure Section XXIII, in dry development systems as described in Research Disclosure Section XXIV and in printing and lithography materials as described in Research Disclosure Section XXV.

The photosensitive materials obtained by the present invention can be processed according to known methods. A developer to be used for the black-and-white processing can contain conventional developing agents such as dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolidones or ascorbic acids.

As color-developing agent, there can be used primary aromatic amine developing agents such as phenylenediamines (e.g., 4-amino-N,N-diethylaniline, 3-methyl-4-amino-N,N-diethylaniline, 4-amino-3-methyl-N-hydroxyethylaniline, 3-methyl-4-amino-N-ethyl-N-hydroxyethylaniline, 3-methyl-4-amino-N-ethyl-N-methanesulfonamidoethylaniline and 4-amino-3-methyl-N-ethyl-N-methoxyethylaniline. In addition, the developing agents described in L.F.A. Mason, *Photographic Processing Chemistry* (Focal Press, 1966), pp. 226–229, as well as those described in U.S. Pat. Nos. 2,193,015 and 2,592,364 may be used.

A photographic emulsion useful in the present invention can be applied to many different silver halide photographic light-sensitive materials due to its high photographic sensitivity, contrast, and fog reduction. For example, it can be used in high speed black-and-white negative films, in X-ray films and in multilayer color negative films.

The following examples further illustrate the invention.

SYNTHESIS EXAMPLE A

Aurous bis(1,4,5-trimethyl-1,2,4-triazolium-3-thiolate) tetrafluoroborate (compound 1)

First the gold(I) starting compound, aurous bis(tetramethylthiourea) tetrafluoroborate, was made as follows. $HAuCl_4.3H_2O$ (0.255 g) was dissolved in 5 mL water and added dropwise to tetramethylthiourea (0.327 g) which was partly dissolved in water. Dark orange and red precipitates formed initially, but after stirring at about 50° to 60° C. the precipitates dissolved and the solution become completely clear and colorless. 0.2 mL $HBF_4$ solution (49% aqueous) was added. After cooling a few hours, white platelets of the product were filtered (84% yield). This intermediate gold(I) compound (0.228 g) was dissolved in 4 mL water by heating to about 60° C., and then added to a room temperature solution of 1,4,5-trimethyl-1,2,4-triazolium-3-thiolate (0.126 g). A white precipitate began to form, and was filtered after standing in the refrigerator a few hours. The product yield was 86%. The product could be recrystallized from hot water. Elemental analysis conformed to the formula for compound 1, and a single-crystal x-ray diffraction study confirmed the structure as a linear, two-coordinate complex with gold-sulfur bond lengths averaging 2.27 angstroms.

SYNTHESIS EXAMPLE B

Aurous bis(1,5-dimethyl-4-amino-1,2,4-triazolium-3-thiolate) tetrafluoroborate (compound 7)

Aurous bis(tetramethylthiourea tetrafluoroborate (0.215 g, prepared as described above) was dissolved in 3 mL water at about 60° C., and then added dropwise to a solution of 1,5-dimethyl-4-amino-1,2,4-triazolium-3-thiolate (0.119 g) also at about 60° C. A white precipitate soon began to form, and after stirring an additional 10 minutes after the addition was complete, the solution was allowed to cool. The product was filtered and washed with alcohol (89% yield). Elemental analysis conformed to the formula of compound 7.

SYNTHESES EXAMPLE C

Aurous bis(1-methyl-4,5-diphenyl-1,2,4-triazolium-3-thiolate) tetrafluoroborate (compound 10)

Aurous bis(tetramethylthiourea) tetrafluoroborate (0.201 g, prepared as described above) was dissolved in 3 mL methanol at room temperature and added dropwise to 1-methyl-4,5-diphenyl-1,2,4-triazolium-3-thiolate (0.216 g) which was partly dissolved in 3 mL methanol at room temperature. The mixture was stirred for 10 minutes after the addition was complete, and then a white powder was filtered (91% yield). This product was soluble in acetone. The elemental analysis conformed to the formula for compound 10.

Solution Stability Example

Compound 1 was dissolved in deionized water at a concentration of $5 \times 10^{-4}$ mole per L. Part of the solution was stored at 40° F. and part was stored at room temperature. Solutions of aurous bis(tetramethylthiourea) tetrafluoroborate (comparison) were prepared and stored in the same fashion. Periodically, aliquots of each solution were withdrawn and examined spectrophotometrically. The solution of compound 1 showed no change in its UV absorption spectrum in either bandshape or intensity for up to 6 months when stored at 40° F. The solution of aurous bis(tetramethylthiourea) tetrafluoroborate stored at 40° F. first began to show changes in absorption bandshape and intensity after four weeks. The solution of compound 1 first began to show changes in absorption bandshape and intensity after 4 weeks storage at room temperature. The solution of the comparison compound underwent gross decomposition after only two days at room temperature, as evidenced by the precipitation of metallic gold in the storage flask as well as large changes in the UV absorption spectrum. Clearly, the novel compounds of the present invention have the practical advantage of greater solution shelf life.

PHOTOGRAPHIC EXAMPLE 1

Silver bromide emulsions containing octahedral grains measuring on average 0.4 microns edge length and contaiing 40 g gelatin per mole Ag were melted at 40° C. and treated with the sensitizers indicated in Table I. The emulsion samples were heated to 65° C., held 15 minutes, cooled, and coated on film support at 200 mg Ag and 600 mg gelatin per $ft^2$ with a gelatin hardener. The dried coatings were exposed sensitometrically at 365 nm for 1/10 second through a step tablet ranging in optical density from 0 to 4 units, and processed for 6 minutes in KODAK Rapid X-ray Developer. The logarithms of the relative speeds were measured at 0.15 optical density above fog. The results below show that use of one of the novel gold(I) compounds in combination with a labile sulfur compound produces a sensitization effect far above that of the sulfur sensitizer by itself.

TABLE I

| Sensitizers (per mole Ag) | Log Relative Speed (Fog) |
| --- | --- |
| None (control) | 1.00 (0.03) |
| 1.24 mg Na$_2$S$_2$O$_3$.5H$_2$O (Comparison) | 1.52 (0.04) |
| 1.24 mg Na$_2$S$_2$O$_3$.5H$_2$O. 2.85 mg compound 1 (Invention) | 2.27 (0.04) |

PHOTOGRAPHIC EXAMPLE 2

Silver bromide emulsions containing cubic grains which measured 0.27 microns in edge length and containing 40 g gelatin per silver mole were melted at 40° C. and treated with the sensitizers listed below. The sulfur sensitizer employed in this example possessed the structure S-1.

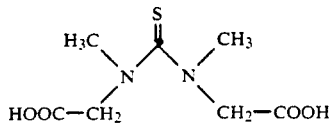

The emulsions were then heated, coated, dried, exposed and processed in the same manner as the emulsions in example 1. The results in the table below show that when used in combination with a sulfur sensitizer, one of the gold(I) compounds of this invention produces a sensitization effect greater than that of the sulfur compound alone.

TABLE II

| Sensitizers (per mole Ag) | Log Relative Speed (Fog) |
| --- | --- |
| None (control) | 1.00 (0.03) |
| 5.9 mg S-1 (Comparison) | 1.58 (0.04) |
| 5.9 mg S-1. 5.3 mg compound 1 (Invention) | 2.13 (0.10) |

PHOTOGRAPHIC EXAMPLE 3

Photographic silver bromoiodide tabular grain emulsions containing silver bromoiodide grains (3 mole % iodide) which had an average circular diameter of 0.9 micron and average thickness of 0.10 micron were spectrally and chemically sensitized according to the following procedures. The emulsion, which also contains 40 g gelatin per mole Ag, was melted at 40° C. and the following ingredients were added per mole of silver: 150 mg NaSCN, 511 mg of a green spectral sensitizing dye having structure S-2 and 145 mg of a green spectral sensitizing dye having structure S-3. The chemical sensitizers indicated in the table below were added next, followed by 30 mg of the finish modifier 3-methyl-1,3-benzothiazolium iodide. The sulfur sensitizer employed in this example possessed the structure S-4. The temperature of the emulsion samples was raised to 65° C. and held for 5 minutes before cooling. 1.75 mg per Ag mole of the stabilizing agent 4-hydroxy-6-methyl-1,3,3a,7-tetraazaindene sodium salt was added as an addendum.

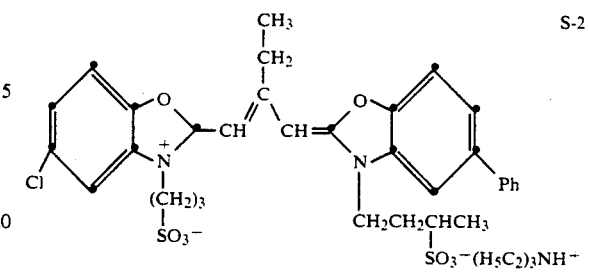

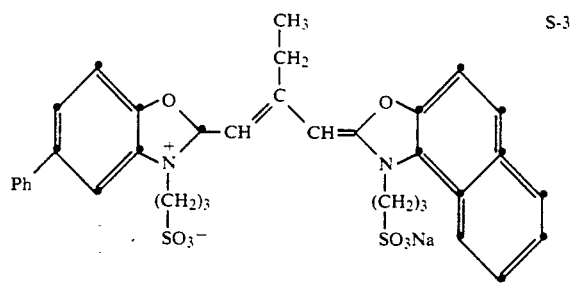

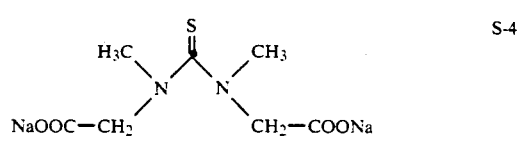

(monohydrate)

Ph herein means phenyl.

The emulsion samples were coated on film support at 75 mg Ag per ft$^2$ and 585 mg gelatin per ft$^2$ with 30 mg per ft$^2$ of a magenta color-forming coupler having structure S-5 and 3 mg per ft$^2$ of a development inhibitor releasing compound having structure S-6. A protective overcoat containing 209 mg gelatin per ft$^2$ with a gelatin hardener was also applied.

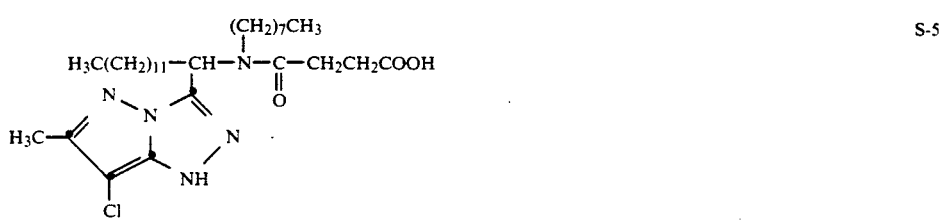

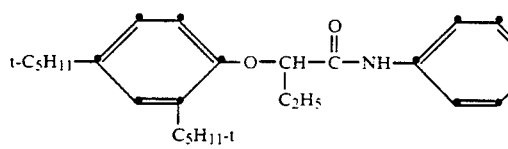
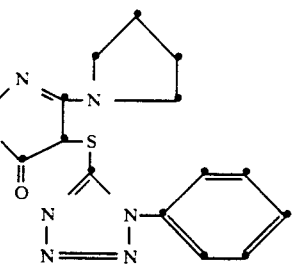

S-6

After drying, the coatings were exposed sensitometrically to a 5500° K. tungsten lamp for 1/50 second through a Kodak Wratten 9 filter (Kodak and Wratten are trademarks of Eastman Kodak Co., U.S.A.) and through a step tablet ranging from 0 to 4 optical density units. After processing the exposed coatings in the C-41 process, the logarithms of the relative speeds were measured at 0.15 optical density units above fog. The results given below show the effect of the novel gold (I) compounds in combination with a sulfur sensitizer over and above the effect of the sulfur sensitizer alone.

TABLE III

| Sensitizers (per mole Ag) | Log Relative Speed (Fog) |
| --- | --- |
| None (control) | 1.00 (0.05) |
| 5.5 mg S-4 (Comparison) | 2.25 (0.16) |
| 5.5 mg S-4, 3.75 mg compound 1 (Invention) | 3.10 (0.11) |

PHOTOGRAPHIC EXAMPLE 4:

Photographic silver bromoiodide tabular grain emulsions containing silver bromide crystals having an average circular diameter of 2.1 microns and a thickness of 0.13 microns and containing 40 g gelatin per mole Ag are spectrally and chemically sensitized by the following procedure. 150 mg NaSCN and 400 mg/Ag mol of the green spectral sensitizing dye having structure S-7 were added to each emulsion at 40° C.

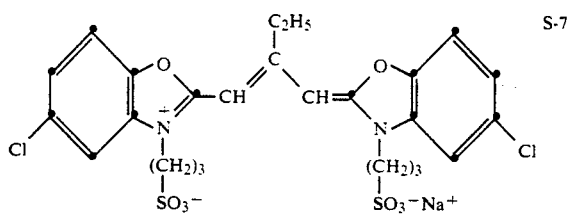

S-7

The finish modifier anhydro-5,6-dimethoxy-3(3-sulfopropyl)benzothiazolium was added at a level of 20 mg/mole Ag. KSeCN at a level of 0.45 mg/mole Ag and the other chemical sensitizers indicated in Table IV were added. Then the temperature was raised to 60° C. and held 60 minutes. After cooling to 40° C., 300 mg KI was added. The emulsions were then coated on film support at 210 mg Ag and 265 mg gelatin per ft² with a gelatin hardener. Two layers of a protective overcoat containing 42 mg gelatin per ft² were applied. The dried coatings were exposed sensitometrically for 1/50 second to a 2850K tungsten lamp through a Corning Filter No. 40-10 and through a step tablet ranging in optical density from 0 to 4. The exposed coatings were then processed in the standard Kodak Xomat process. The logarithms of the relative speeds were determined at 1.0 optical density above fog. In addition, the following test was carried out to measure the sensitivity to red safelights. From the sensitometric data previously obtained for the tungsten exposures through the Corning 40-10 Filter, the exposure necessary to produce an optical density of 0.60 above fog was determined. This exposure was first applied to the coatings. Next, half of each coating was masked off to prevent any further exposure and then each strip was subjected to an additional red safelight exposure for 8 minutes which was produced by placing a 15 watt incandescent bulb and a GBX filter 48 inches from the coatings. The coatings were processed as before. The difference in optical density between that part of the coating which was additionally exposed to the safelight and that part which was not, constitutes a measure of the safelight response. The sensitometric results are listed in Table IV.

TABLE IV

| Sensitizer | Log Rel. Speed | Contrast | Safelight Response |
| --- | --- | --- | --- |
| 5 mg Na₃Au(S₂O₃)₂—2H₂O (Comparison) | 1.00 | 2.77 | 0.12 |
| 2.4 mg Na₂S₂O₃—5H₂O, 5.5 mg compound 1 (Invention) | 1.02 | 2.94 | 0.02 |

It is seen from this data that a compound of the present invention used in combination with one molar equivalent of sulfur sensitizer results in a lower sensitivity to red safelight and a higher contrast compared to sensitization with an amount of aurous dithiosulfate which is equivalent in number of moles of gold but which inherently contains two molar equivalents of S sensitizer.

PHOTOGRAPHIC EXAMPLE 5:

Silver chloride emulsions containing cubic grains with an average edge length of 0.63 micron, which were made in the presence of thioether silver halide ripeners of the type described in McBride U.S. Pat. No. 3,271,157 and containing 40 g gelation per Ag mole were chemically and spectrally sensitized in the following manner. The chemical sensitizers listed in Table V were added to the emulsion samples at 40° C. Then the temperature was raised to 60° C. and held 20 minutes. 250 mg/Ag mole of a blue spectral sensitizing dye having structure S-8 was added. The emulsion samples were then doctored with 92 mg/mole Ag of the antifoggant 1-(3-acetamidophenyl)-5-mercaptotetrazole sodium salt and 218 mg KBr/mole Ag. The emulsions were coated on paper support at 26 mg Ag/ft² and 144 mg gelatin/ft² with 100 mg per mole Ag of a yellow color-forming coupler having the structure S-9. An overcoat containing 100 mg gelatin/ft² was applied with a hardener.

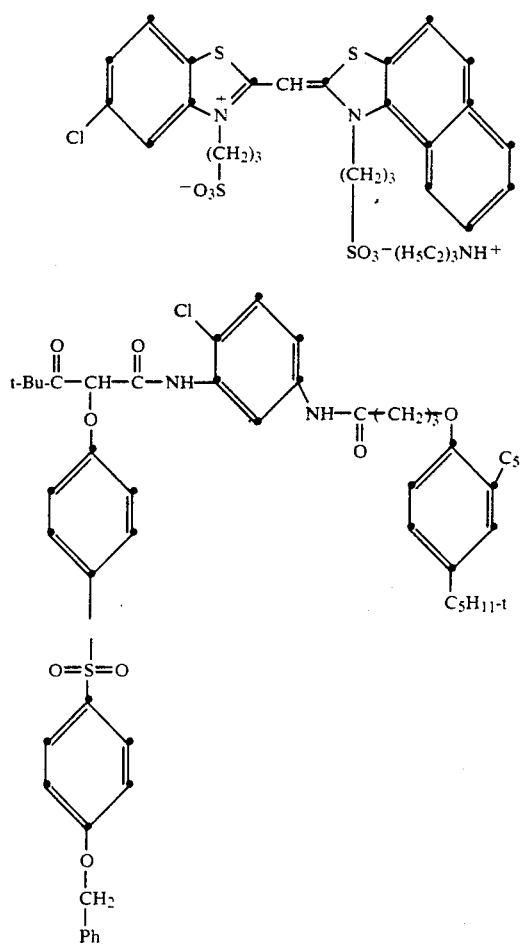

The dried coatings were exposed sensitometrically to a 3000K tungsten source for 0.1 second through a step tablet ranging in optical density from 0 to 4 units. Processing was done through a standard Kodak RA4 process. The logarithms of the relative speeds were determined at a density of 1.0 above fog. The sensitometric responses are given below.

TABLE V

| Sensitizer | Log Rel. Speed | Contrast |
| --- | --- | --- |
| 0.63 mg Na$_3$Au(S$_2$O$_3$)$_2$— 2H$_2$O (Comparison) | 158 | 193 |
| 0.30 mg Na$_2$S$_2$O$_3$— 5H$_2$O, 0.79 mg compound 1 (Invention) | 167 | 211 |

It is seen from this data that a compound of the present invention used in combination with one molar equivalent of sulfur sensitizer results in a higher contrast compared to sensitization with aurous dithiosulfate, which inherently contains two equivalents of the sulfur sensitizer thiosulfate.

The invention has been described in detail with particular reference to preferred embodiments thereof, but it will be understood that variations and modifications can be effected within the spirit and scope of the invention.

What is claimed is:

1. A gold (I) compound of the formula AuL$_2^+$X$^-$ wherein:
L is

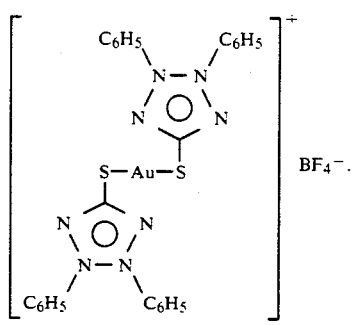

R$_1$ is CH$_3$
R$_2$ is CH$_3$,CH$_2$CH=CH$_2$, CH$_2$CH$_2$OCH$_3$,NH$_2$, C$_4$H$_9$, C$_6$H$_{11}$ or C$_6$H$_5$
R$_3$ is CH$_2$ or C$_6$H$_5$; and
X$^-$ is BF$_4^-$,I$^1$, Br$^-$, or Cl$^-$.

2. The compound of claim 1 wherein
R$_2$ is CH$_3$,
R$_3$ is CH$_3$, and
X$^-$ is BF$_4^-$.

3. The compound of claim 1 wherein
R$_2$ is CH$_2$CH=CH$_2$,
R$_3$ is CH$_3$, and
X$^-$ is BF$_4^-$.

4. The compound of claim 1 wherein
R$_1$ is CH$_3$,
R$_2$ is CH$_2$CH$_2$OCH$_3$,
R$_3$ is CH$_3$, and
X$^-$ is BF$_4^-$.

5. The compound of claim 1 wherein
R$_1$ is CH$_3$,
R$_2$ is HH$_2$,
R$_3$ is CH$_3$, and
X$^-$ is BF$_4^-$.

6. The compound of claim 1 wherein
R$_1$ is CH$_3$,
R$_2$ is C$_6$H$_5$,
R$_3$ is C$_6$H$_5$, and
X$^-$ is BF$_4^-$.

7. A gold(I) compound of the formula

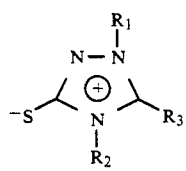

8. A gold(I) compound of the formula AuL(L$^1$)+X$^-$ wherein:
L is

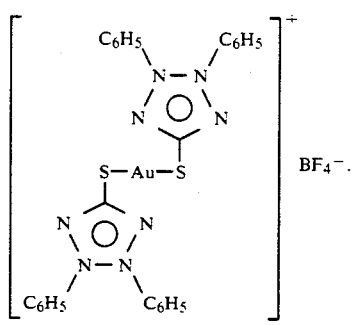

and
R$_1$ is CH$_3$,
R$_2$ is CH$_3$ or CH$_2$CH=CH$_2$
R$_3$ is CH$_3$
L$^1$=P(CH$_3$)$_3$
X$^-$ is Cl$^-$ or BF$_4^-$.

* * * * *

UNITED STATES PATENT AND TRADEMARK OFFICE
CERTIFICATE OF CORRECTION

PATENT NO. : 5,220,030
DATED : June 15, 1993
INVENTOR(S) : J. C. Deaton

It is certified that error appears in the above-indentified patent and that said Letters Patent is hereby corrected as shown below:

In column 14, line 13, delete "$X^-$ is $BF_4^-$, $1^1$" and insert --$X^-$ is $BF_4^-$, $1^-$--.

Signed and Sealed this

Twenty-second Day of February, 1994

Attest:

BRUCE LEHMAN

*Attesting Officer*     *Commissioner of Patents and Trademarks*